(12) United States Patent
Cronin et al.

(10) Patent No.: US 6,577,903 B1
(45) Date of Patent: Jun. 10, 2003

(54) THERMAL SENSOR POSITIONING IN A MICROWAVE WAVEGUIDE

(75) Inventors: Nigel Cronin, Bath (GB); Ian Bruce Feldberg, Petersfield (GB)

(73) Assignee: Microsulis PLC, Waterkiivukk (GB)

( * ) Notice: Subject to any disclaimer, the term of this patent is extended or adjusted under 35 U.S.C. 154(b) by 0 days.

(21) Appl. No.: 09/674,782

(22) PCT Filed: May 5, 1999

(86) PCT No.: PCT/GB99/01400

§ 371 (c)(1),
(2), (4) Date: Dec. 13, 2000

(87) PCT Pub. No.: WO99/56643

PCT Pub. Date: Nov. 11, 1999

(30) Foreign Application Priority Data

May 6, 1998  (GB) .............................................. 9809536

(51) Int. Cl.[7] ................................................. A61F 2/00
(52) U.S. Cl. ........................ 607/102; 607/103; 219/690
(58) Field of Search ................................. 607/101, 102, 607/103, 105, 154; 219/690, 710, 712

(56) References Cited

U.S. PATENT DOCUMENTS 5,601,367 A * 2/1997 Nara ........................... 374/183

FOREIGN PATENT DOCUMENTS

WO       WO 95/04385       * 2/1995

* cited by examiner

Primary Examiner—Edward K. Look
Assistant Examiner—Michael Leslie
(74) Attorney, Agent, or Firm—Reising, Ethington, Barnes, Kisselle, Learman & McCulloch, P.C.

(57) ABSTRACT

A method of positioning on a microwave waveguide a sensor (20) including an elongate metallic element (23, 24) comprising: selecting a tubular waveguide (12); determining the general orientation of the magnetic field (3) generated during microwave transmission; and positioning the elongate metallic element (20, 23, 24) substantially parallel to the orientation of the magnetic field (3). Connections (23, 24) of the sensor (20) extend longitudinally of the waveguide (12) and are connected to the outer wall (25) of the waveguide and the central conductor (16) of the coaxial cable (15) that powers the waveguide.

10 Claims, 3 Drawing Sheets

THERMAL SENSOR POSITIONING IN A MICROWAVE WAVEGUIDE

TECHNICAL FIELD

This invention relates to positioning a sensor on a microwave device, especially an applicator for treatment of a body by means of microwave electromagnetic energy, and also relates to an applicator including a sensor positioned thereon.

In our prior published application No. WO95/04385, the contents of which are incorporated herein by reference, we have disclosed apparatus for the treatment of menorrhagia which involves applying microwave electromagnetic energy at a frequency which will be substantially completely absorbed by the endometrium, monitoring the operating temperature to ensure that the endometrium tissue is heated to about 60° and maintaining the application of the microwave energy for a period of time sufficient to destroy the cells of the endometrium.

The temperature is therefore important and a temperature sensor in the form of a thermocouple is used to monitor the temperature on an ongoing basis during application.

The problem which arises is that a thermocouple is constructed of metal and the application of microwave energy tends to cause direct heating of the thermocouple which leads to errors in the temperature readings. This general problem is discussed in S. B. Field and J. W. Hand "An Introduction to the Practical Aspects of Clinical Hyperthermia" at pages 459–465. As a result of the problems encountered with metallic sensors, it has been the practice to take readings either when the power is off, which precludes real-time measurement, or measurement has been by non-metallic sensors, such as fibre-optic sensors, which are much more expensive.

Microwave electromagnetic energy can be propagated either by coaxial waveguide or by tubular waveguide typically of circular cross-section.

DISCLOSURE OF THE INVENTION

The invention consists in a method of positioning on a microwave waveguide a sensor including an elongate metallic element comprising: selecting a tubular waveguide; determining the general orientation of the magnetic field generated during microwave transmission; and positioning the elongate metallic element substantially parallel to the orientation of the magnetic field.

With this arrangement, current should not be induced in the metallic element by the magnetic field and there should therefore be little or no interference with the parameter being sensed. Typically, the sensor will be a thermocouple sensing temperature and the inherent danger is interference by current flowing in the metal sheath of the thermocouple.

The invention also consists in a microwave applicator comprising a tubular waveguide which, on transmission of microwaves, generates an electric field orientated substantially perpendicular to the waveguide wall and a magnetic field substantially perpendicular to the electric field, and a sensor including an elongate metallic element, said elongate metallic substantially no current is induced in the metallic element of the sensor which would otherwise cause distortion.

DESCRIPTION OF THE DRAWINGS

The invention wide now be described by way of example with reference to the accompanying drawings in which:

In FIG. 1, the diagrammatic cross-section of a coaxial waveguide is shown where (1) is the centre conductor and (2) is the outer conductor. A coaxial waveguide propagates microwave energy in the TEM mode, and both the magnetic field (3) and the electric field (4) are always perpendicular to the axis (the centre conductor). Since currents (5) always flow at right angles to the magnetic field they will always flow along the coaxial waveguide or any other metal structure which they come into contact with. Therefore, wherever one places a metallic temperature sensor (6) on a coaxial derived applicator, current will flow in the metallic sensor because the sensor is perpendicular to the magnetic field. (6) on a coaxial derived applicator, current will flow in the metallic sensor because the sensor is perpendicular to the magnetic field.

In FIG. 2, a diagrammatic cross-section of a circular waveguide (7) is shown where magnetic field lines (3) and the electric field lines (4) are illustrated for the transverse electric mode TE11. In this arrangement, the electric field is always perpendicular to the waveguide wall (8) and the magnetic field is always perpendicular to the electric field.

FIG. 3 shows a diagrammatic top view of field distributions along the circular waveguide (7) of FIG. 2. Magnetic field loops (3) are separated by regions of high electric field (4). Note that the magnetic field loops are parallel to the sides of the waveguide wall (8).

FIG. 4 shows a diagrammatic side view of current flow in the walls of the circular waveguide (7) of FIG. 2. Here one can see that if a metallic sensor (6) is placed substantially parallel to the magnetic field at the side of the waveguide wall (8), then all current paths will cross the sensor and there will be no generated current flow in the sensor (6).

We have found that by placing the thermocouple sensor (6) substantially parallel to the magnetic field (3) at the wall of the waveguide (8), then substantially no current flows in the metallic elements of the sensor (6) and real-time temperature monitoring is possible without any substantial distortion.

The invention will now be further described by reference to FIG. 5, which is a diagrammatic side elevation of a microwave applicator including a temperature sensing thermocouple positioned in accordance with the present invention.

Figure 1:
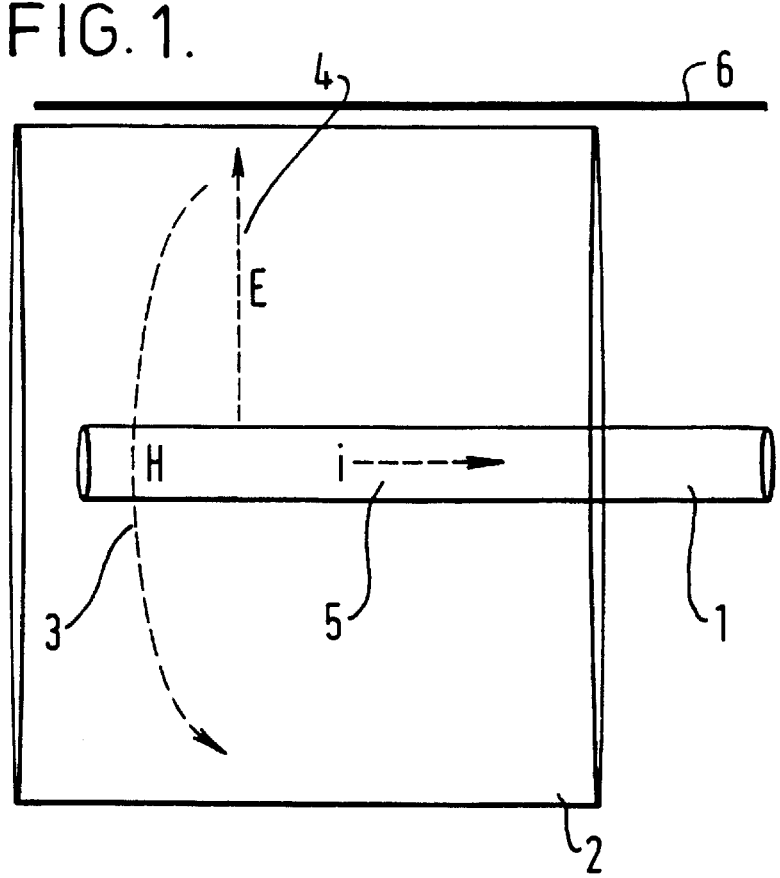
FIG. 1 is a diagrammatic side elevation of a coaxial waveguide operating in the TEM mode showing the electric and magnetic fields.
Figure 2:
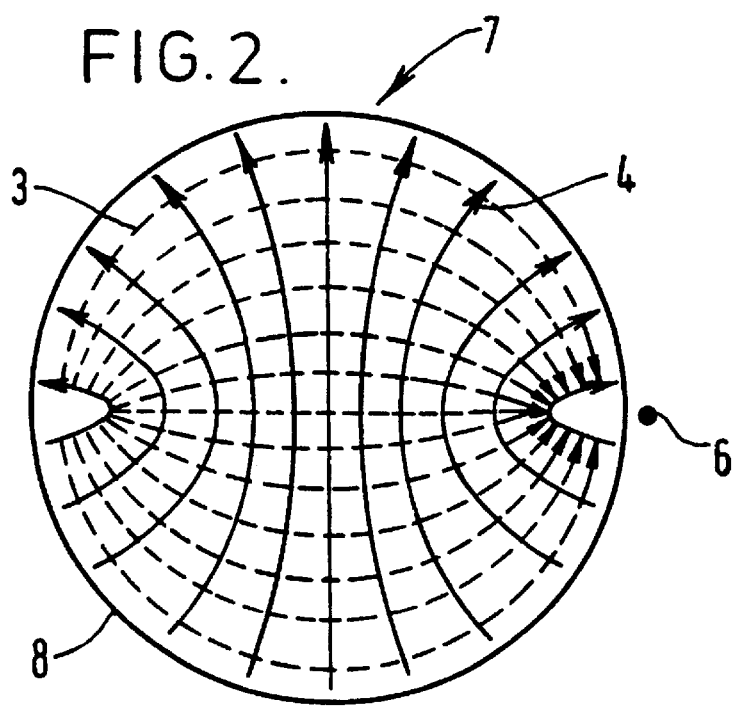
FIG. 2 is a diagrammatic cross-section of a circular waveguide according to the invention operating in the TE11 mode.
Figure 3:
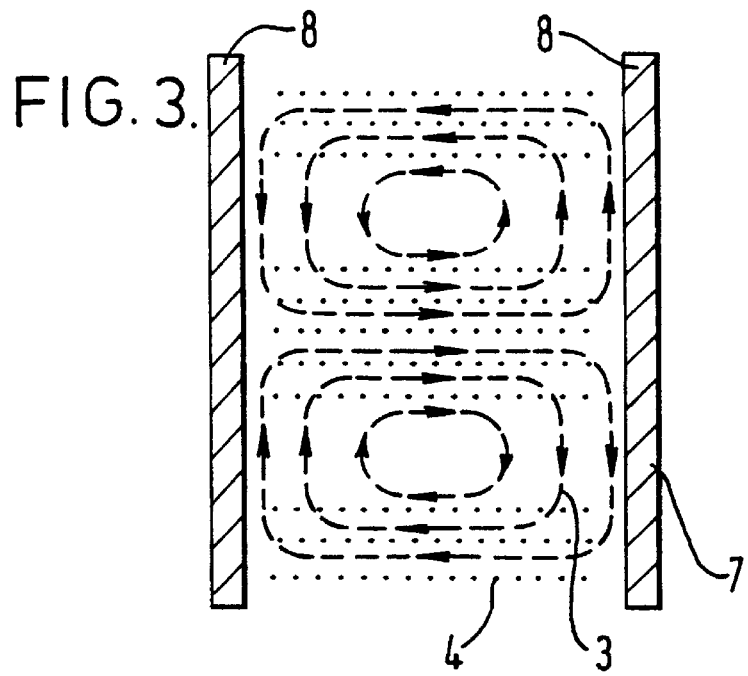
FIG. 3 is a diagrammatic plan view of the circular waveguide of FIG. 2.
Figure 5:
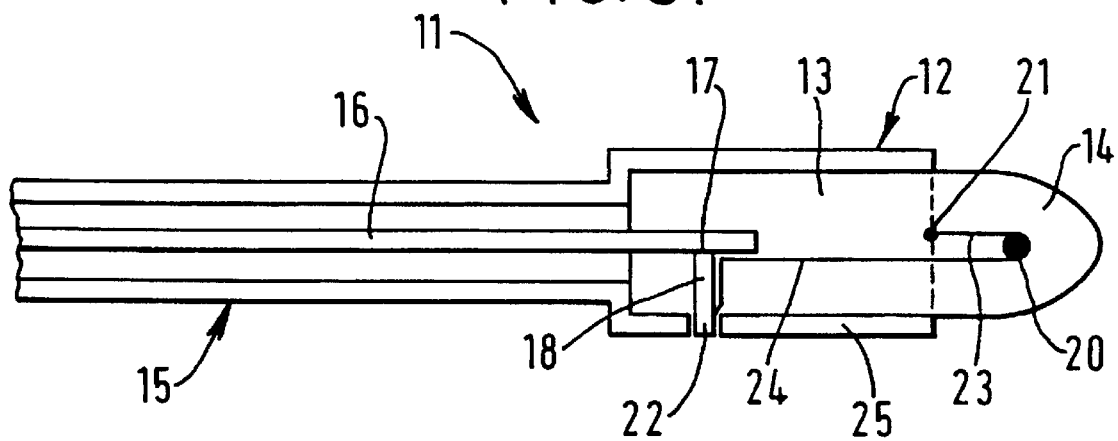
FIG. 5 is a diagrammatic side elevation of a microwave applicator a according to the invention.

In FIG. 5, a microwave applicator (11) has a circular waveguide (12) filled with a dielectric material (13). The waveguide (12) terminates short of the end of the applicator (11) providing an exposed portion (14) which forms a radiating antenna tip for the microwave energy. Towards the end of the applicator remote from the radiating tip (14), there is a coaxial feed cable (15) having an inner conductor (16) which directly excited the dielectric filled waveguide (12) via an in-line transition (17). The inner conductor (16)

passes to the centre of the dielectric material (13) and a lateral conductor (18) which passes from the central conductor through the outer waveguide wall (12) forms a microwave break allowing the transition to cause the microwaves to launch into the dielectric material (13) as shown in FIGS. 1 to 3. The conductor (18) is insulated by insulation as it passes through the outer conductor formed by the waveguide wall (12).

Figure 4:
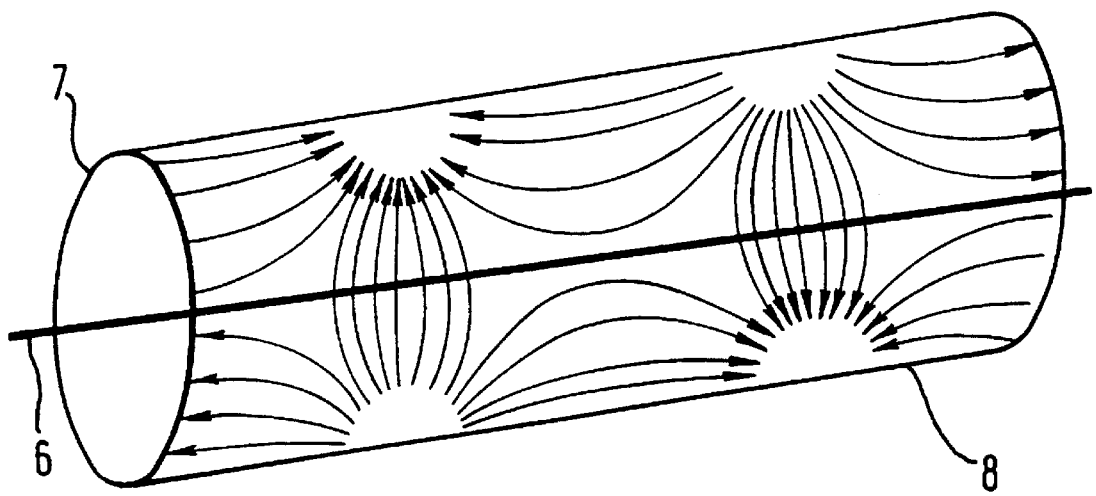
FIG. 4 is a diagrammatic side view of the circular waveguide of FIG. 2 showing the current flow in the walls.

The sensor positioned in accordance with the invention is a thermocouple (20) located on the outside of the radiating tip (14) for sensing the operating temperature. In accordance with the invention, the thermocouple (20) is positioned substantially parallel to the orientation of the magnetic field generated by the circular waveguide (12) when propagating microwaves, that is, along the line of the element (6) in FIGS. 2 and 4. Moreover, in order to avoid additional wiring, the thermocouple (20) is directly connected by a connection (23) to the outer conductor waveguide wall at (21) and by a connection (24) to the lateral conductor (18) at (22). The connections (23,24) extend parallel to one another in a plane through the axis of the waveguide, and the one (23) terminates at (21) and the other (24) extends outside the wall (12) as far as the perpendicular plane through (22), and then runs round the circumference of the wall (12) to the conductor (18) at (22). R Accordingly, the thermocouple signal passes out along the same coaxial cable bringing the microwave power to the radiating tip (14). Conventional circuitry (not shown) is used to sense and extract the DC signal.

The location of the thermocouple itself, at a position where there is no induced current in operation, enables real-time sensing of the operating temperature without any substantial distortion.

Although not shown, the applicator (11) is provided with a microwave-transparent protective coating of pTFE or other suitable material. The temperature sensor sensing thermocouple (20) is provided between the coating and the dielectric material as well as being insulated from the dielectric material.

What is claimed is:

1. A microwave applicator comprising a tubular waveguide which, on transmission of microwaves in transverse electromagnetic modes, particularly in the $TE_{11}$ mode, generates an electric field orientated substantially perpendicular to the waveguide wall and a magnetic field substantially perpendicular to the electric field, and a sensor including at least one elongate conductive element wherein said element is positioned on the waveguide so as to be substantially parallel to said magnetic field during said microwave transmission, and to be in a region in which said magnetic field induces minimum current in said element, thereby to minimise induced heating.

2. A microwave applicator as claimed in claim 1, in which the dielectric material extends from an output end of the waveguide so as to form an antenna to emit microwave radiation, the sensor being located on a side of the antenna.

3. A microwave applicator as claimed in claim 2, in which said element comprises sensor connections which extend parallel to one another, a first sensor connection being connected, to an outer wall of the waveguide, and a second sensor connection being connected to a conductor of a power input.

4. A microwave applicator as claimed in claim 3, in which the power input comprises a coaxial cable and said conductor comprises an inner conductor of the coaxial cable which extends into said dielectric material.

5. A microwave applicator as claimed in claim 4, in which a lateral conductor extends radially from said conductor, and said second sensor connection is connected to an outer end of the lateral conductor.

6. A microwave applicator as claimed in claim 5, in which the outer end of the lateral conductor extends through an aperture in the outer wall of the waveguide and is electrically insulated from it.

7. A microwave applicator as claimed in claim 5, in which said second sensor connection extends longitudinally of the waveguide from the sensor and then circumferentially of the outer wall of the waveguide to the outer end of the lateral conductor.

8. A method of positioning a sensor including an elongate conductive element on a microwave waveguide comprising: selecting a tubular dielectric filled waveguide; determining the general orientation of a magnetic field generated by the waveguide during microwave transmission; and positioning the elongate conductive element substantially parallel to the orientation of the magnetic field.

9. A method as claimed in claim 8, in which the waveguide is powered by a coaxial cable and in which the output of the sensor is connected to the coaxial cable.

10. A microwave applicator comprising a tubular waveguide filled with dielectric material extending from an output end of the waveguide to form an antenna; a power input comprising an inner conductor of a coaxial cable which extends into the dielectric material to generate microwaves in transverse electromagnetic modes, particularly in the $TE_{11}$ mode, from which microwave energy is emitted, the microwaves within the waveguide generating an electric field orientated substantially perpendicular to the waveguide wall and a magnetic field substantially perpendicular to the electric field; and a sensor located on a side of the antenna comprising at least one elongate conductive element extending substantially parallel to the magnetic field in a region in which said magnetic field induces minimum current in said element.

* * * * *

UNITED STATES PATENT AND TRADEMARK OFFICE
CERTIFICATE OF CORRECTION

PATENT NO.    : 6,577,903 B1                                                                 Page 1 of 1
DATED         : June 10, 2003
INVENTOR(S)   : Nigel Cronin It is certified that error appears in the above-identified patent and that said Letters Patent is hereby corrected as shown below:

Column 1,
Line 61, after "said elongate metallic" insert -- element being positioned on the waveguide so as to extend substantially parallel to the magnetic field during mirowave transmission, whereby --

Column 2,
Line 5, after "operating in the" delete "TE11" and insert -- $TE_{11}$ --
Line 14, after "applicator" delete "a"
Lines 26-29, delete repeated sentence starting with "(6)"
Line 33, after "electric mode" delete "TE11" and insert -- $TE_{11}$ --

Column 3,
Line 25, before "Accordingly" delete "R"
Line 35, before "TFE" delete "p" and insert -- P --

Signed and Sealed this

Twenty-first Day of October, 2003

JAMES E. ROGAN
*Director of the United States Patent and Trademark Office*